United States Patent [19]

Renner et al.

[11] Patent Number: 4,549,008
[45] Date of Patent: Oct. 22, 1985

[54] NOVEL TETRAGLYCIDYL ETHERS

[75] Inventors: Alfred Renner, Muntelier; Peter Grütter, Aarau; Rolf Hügi, Ramlinsburg, all of Switzerland

[73] Assignee: Ciba-Geigy Corporation, Ardsley, N.Y.

[21] Appl. No.: 640,281

[22] Filed: Aug. 13, 1984

[30] Foreign Application Priority Data

Aug. 23, 1983 [CH] Switzerland .......................... 4577/83
Apr. 18, 1984 [CH] Switzerland .......................... 1947/84

[51] Int. Cl.[4] .................... C08G 59/24; C08G 59/32
[52] U.S. Cl. .................... 528/220; 528/226; 528/229; 528/365; 528/407; 549/560
[58] Field of Search .............. 528/220, 226, 229, 365, 528/407; 549/560

[56] References Cited

U.S. PATENT DOCUMENTS

| | | |
|---|---|---|
| 2,462,031 | 2/1949 | Wittcoff . |
| 3,138,618 | 6/1964 | Nikles et al. .......................... 549/560 |
| 3,298,981 | 1/1967 | Fry et al. .......................... 549/560 |
| 3,395,128 | 7/1968 | Hale et al. .......................... 549/560 |

OTHER PUBLICATIONS

H. Lee and K. Neville, "Handbook of Epoxy Resins", McGraw-Hill, New York, 1967, pp. 2-16.

*Primary Examiner*—Earl Nielsen
*Attorney, Agent, or Firm*—Luther A. R. Hall

[57] ABSTRACT

Novel tetraglycidyl ethers of the formula

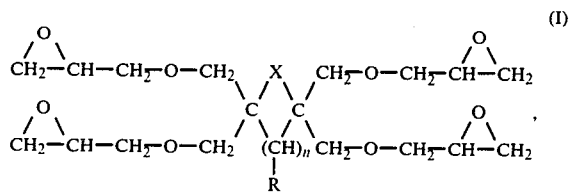

wherein X is a group

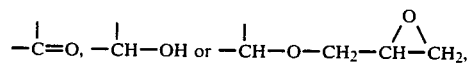

R is hydrogen or methyl, and n is an integer from 2 to 4.

The novel tetraglycidyl ethers can be used in curable mixtures, together with a curing agent for epoxide resins, in particular for the protection of surfaces.

9 Claims, No Drawings

NOVEL TETRAGLYCIDYL ETHERS

The present invention relates to novel tetraglycidyl ethers, and to their use in curable mixtures.

Polyglycidyl ethers of cycloaliphatic alcohols are known. Thus, for example, the diglycidyl ether of 2,2-bis(p-hydroxycyclohexyl)propane, known as hydrogenated bisphenol-A, is mentioned in H. Lee, K. Neville: Handbook of Epoxy Resins (1967), McGraw Hill Co., New York, pages 2-16.

A need for novel highly reactive, cycloaliphatic epoxide resins which have good technical properties, and of which the starting products for the synthesis are readily available, has nevertheless hitherto still existed. There have however now been found novel cycloaliphatic epoxide resins which meet these requirements.

The present invention relates therefore to tetraglycidyl ethers of the formula I

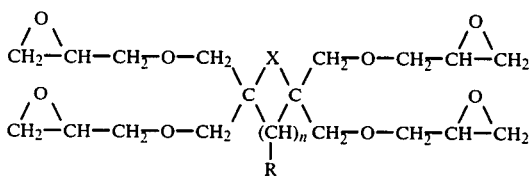

wherein X is a group

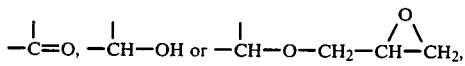

R is hydrogen or methyl, and n is an integer from 2 to 4.

Preferred tetraglycidyl ethers of the formula I are those wherein X is the group

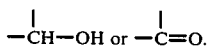

Likewise preferred are tetraglycidyl ethers of the formula I wherein R is hydrogen.

n is preferably 2 or 3.

Particularly preferred is the tetraglycidyl ether of the formula I wherein X is the group

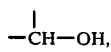

R is hydrogen, and n is 3.

The tetraglycidyl ethers of the formula I according to the invention are obtained for example by reacting a compound of the formula II

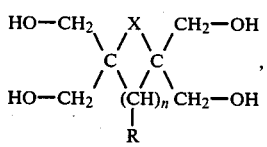

wherein X, R and n have the meanings defined in the foregoing, with an epihalohydrin, in the presence of a catalyst, to give the corresponding tetrahalohydrin ether, and dehydrohalogenating this in the presence of an alkali metal hydroxide.

Suitable epihalohydrins are for example epibromohydrin and especially epichlorohydrin.

Catalysts suitable for the reaction of the compound of the formula II with epihalohydrin are in particular Lewis acids, for example: $AlCl_3$, $SbCl_5$, $SnCl_4$, $FeCl_3$, $ZnCl_2$ and $BF_3$.

The reaction of the compounds of the formula II with epihalohydrin in the presence of a Lewis acid is preferably performed in the presence of an inert organic solvent. The solvent used is preferably 1,4-dioxane.

In place of pure dioxane, it is also possible to use a solvent mixture of at least 30 percent by weight of dioxane and another organic solvent which has a boiling point of at least 70° C. and which is not reactive with epihalohydrin. Suitable organic solvents which can be used in combination with dioxane, but in an amount not exceeding 70 percent by weight of the solvent mixture, are for example: n-heptane, n-octane, 1,2-dichloroethane, 1,2,2-trichloroethylene, benzene, toluene, xylene, chlorobenzene, methyl ethyl ketone, ethyl acetate and n-butyl acetate.

The reaction is preferably performed in the presence of $SnCl_4$ as catalyst in 1,4-dioxane.

The epihalohydrin is used in at least stoichiometric amounts or in a slight excess, preferably 4-5 mols.

Suitable catalysts for the reaction with epihalohydrins are also quaternary ammonium salts, preferably salts of ammonium halides, for example tetramethylammonium chloride, tetraethylammonium bromide or benzyltrimethylammonium bromide. The preferred ammonium halide is tetramethylammonium chloride. The quaternary ammonium salts are preferably used in the form of aqueous solutions.

The reaction of the compounds of the formula II with the epihalohydrin in the presence of an ammonium salt is preferably performed in the corresponding epihalohydrin as solvent. There are preferably used 2 to 10 mols of epihalohydrin per hydroxyl group in the formula II.

The reaction of the compounds of the formula II with an epihalohydrin to the corresponding tetrahalohydrin ethers can be carried out also in the presence of alkali metal hydroxides, for example potassium or sodium hydroxide. The alkali metal hydroxides can be used for example in the form of concentrated aqueous solutions.

Dehydrohalogenation is performed advantageously by means of an alkali metal hydroxide, preferably NaOH, which is used in an equivalent amount or in a slight excess. It is advantageous to use anhydrous sodium hydroxide or a concentrated aqueous solution thereof, preferably a 50% sodium hydroxide solution. Accordingly, alkali metal hydroxides are suitable both for the reaction of the compounds of the formula II with epihalohydrins and for the subsequent dehydrohalogenation.

In some cases, for example when quaternary ammonium salts are used for the reaction, the glycidylation is performed advantageously with the azeotropic removal of water in the simultaneous presence of the catalyst and the sodium hydroxide solution. The sodium hydroxide solution is added during the azeotropic removal of water under reduced pressure. Water, which serves as solvent for the NaOH, and that formed during the reaction, is in this manner continuously removed from the reaction mixture.

The salt formed during the reaction, for example sodium chloride, is washed out, filtered off or removed by centrifuging. Unreacted epihalohydrin is optionally distilled off in vacuo.

The compounds of the formula II which are used as starting compounds can be produced for example by the process described in the U.S. Pat. No. 2,462,031. The epihalohydrin is obtainable commercially or can be produced by known methods.

The tetraglycidyl ethers according to the invention are suitable, in admixture with customary curing agents and optionally with epoxide resins based on bisphenol-A, for example as coating, casting, dipping or impregnating resin components. The present invention relates therefore also to curable mixtures containing a tetraglycidyl ether of the formula I and a curing agent for epoxide resins.

The tetraglycidyl ethers according to the invention are in general very light-coloured resins which give, on being cured, excellent coatings resistant to light and to weather, and having for example a high gloss retention.

Customary curing agents are for example carboxylic acid anhydrides, compounds having several mobile hydrogen atoms, such as polyamines, polyamidoamines, polythiols and polybasic acids. The conversion into the insoluble and infusible state is effected if necessary by the action of heat. Also anionic polymerisation catalysts, for example $BF_3$ and complexes thereof, or cationic, for example tertiary, amines and imidazoles, are suitable for inducing and accelerating curing.

With respect to the majority of the curing agents mentioned, the compounds according to the invention prove to be more reactive than known glycidyl ethers of polyvalent phenols, for example resorcinol, optionally hydrogenated bisphenol-A and novolaks. Their high reactivity, combined with the good flexibility of the cured products obtained therewith, render the compounds of the invention particularly suitable for lacquer resins, casting resins, dipping resins and impregnating resins. By virtue of the high functionality of the compounds, it is possible to obtain, after curing, a high crosslinking density. There can be obtained for example, with aliphatic or cycloaliphatic polyamines, coatings and films having excellent resistance to chemicals.

To the curable epoxide resin mixtures according to the invention, there can be added the customary additives, such as active diluents for lowering the viscosity, or extenders, fillers and reinforcing agents, as well as pigments, dyes, plasticisers, levelling agents, thixotropic agents and flame-retarding substances.

Especially for application in the lacquer field, the novel polyglycidyl ethers can moreover be partially or completely esterified in a known manner with carboxylic acids, such as in particular with higher unsaturated fatty acids. It is also possible to add to such lacquer resin formulations other curable plastics, for example phenoplasts or aminoplasts.

The curable mixtures can be produced in the customary manner with the aid of known mixing apparatus (stirrers, kneaders or rollers, and so forth).

The curable epoxide resin mixtures according to the invention are used in particular in the field of surface protection, in the electrical industry, in lamination processes and in the building trade. They can be applied as a formulation adapted to suit the specific purpose of application, in the unfilled or filled conditions, optionally in the form of solutions or emulsions, as coating compounds or as lacquers, as (whirl)-sintering powders, moulding compounds, injection-moulding formulations, dipping resins, casting resins, impregnating resins, binders and adhesives, as tool resins, electrical insulating materials, laminating resins, sealing compounds and stopping materials, flooring materials, and binders for mineral aggregates. Their preferred uses are for surface protection and for casting resins.

Except where otherwise stated in the following Examples, parts are parts by weight, and percentages are percent by weight.

PRODUCTION EXAMPLES

EXAMPLE 1

Tetraglycidyl ether of 2,2,6,6-tetramethylolcyclohexanol 225 parts of tetramethylolcyclohexanol are suspended in 420 parts of dioxane; 18 parts of tin tetrachloride are then added and the temperature is raised to 100° C., in the course of which a homogeneous solution is formed. There are subsequently added dropwise, with stirring, 564 parts of epichlorohydrin in such a manner that the solution always gently boils. The solution is afterwards refluxed for 2 hours; the dioxane is then distilled off, and the residue is dissolved in 1080 parts of toluene. This solution is distilled under a reduced pressure of about 0.15 bar through a water separator and, in the course of 5 hours, 396 parts of a 50% aqueous sodium hydroxide solution are added dropwise at 55° C., water being continuously removed during this process. After the addition of the sodium hydroxide solution has been completed, the azeotropic distillation is continued for 30 minutes. The solution is cooled to 25° C., and is washed with water and then with a 5% $NaHSO_4$ solution. The reaction mixture is dried over $Na_2SO_4$; the toluene is distilled off under reduced pressure, and the residue is clarified by filtration at 80° C.

| | |
|---|---|
| yield: | 440 parts (98% of theory) |
| viscosity at 25° C.: | 2.61 Pa · s |
| epoxide content: | 7.4 equiv./kg |
| $Cl_{total}$: | 6.44% |
| $Cl_{hydrolysable}$: | 0.047% |
| colour value according to Gardner and Holt: | 1-2. |

EXAMPLE 2

Tetraglycidyl ether of 2,2,6,6-tetramethylolcyclohexanol 110 parts of tetramethylolcyclohexanol and 15 parts of a 50% aqueous solution of tetramethylammonium chloride are dissolved at 100° C. in 1850 parts of epichlorohydrin. The solution is cooled to 55° C. and, by a lowering of the pressure to about 0.15 bar, a distillation of epichlorohydrin through a water separator is initiated. In the course of 3 hours, 220 parts of a 50% aqueous sodium hydroxide solution are added dropwise, water being at the same time continuously removed by distillation. After the separation of water has been completed, distillation is continued for 1 hour with the feeding back of epichlorohydrin; the reaction mixture is then cooled to 30° C., the precipitated sodium chloride is removed by filtration and is washed with epichlorohydrin. The combined epichlorohydrin solution is washed with 150 parts by volume of a 10% aqueous $NaH_2PO_4$ solution; it is subsequently washed with water and dried over $Na_2SO_4$. The epichlorohydrin is then distilled off in a rotary evaporator and dried at 140° C. at 0.02 bar. The residue is clarified by filtration through cellite.

| yield: | 192 parts (77% of theory) |
|---|---|
| viscosity at 25° C.: | 5.9 Pa · s |
| epoxide content: | 7.3 equiv./kg |
| $Cl_{total}$: | 0.75% |
| $Cl_{hydrolysable}$: | 0.085% |
| colour value according to Gardner and Holt: | 3. |

EXAMPLE 3

Tetraglycidyl ether of 2,2,6,6-tetramethylolcyclohexanone

According to the procedure of Example 2, 110 parts of 2,2,6,6-tetramethylolcyclohexanone are reacted, in the presence of 12 parts of 50% aqueous tetramethylammonium chloride, with 1100 parts of epichlorohydrin and 176 parts of a 50% aqueous sodium hydroxide solution. The product is obtained in the form of a yellow oil.

| yield: | 146.5 parts (66% of theory) |
|---|---|
| epoxide content: | 6.57 equiv./kg |
| $Cl_{total}$: | 1.27% |
| $Cl_{hydrolysable}$: | 0.15%. |

EXAMPLE 4

Tetraglycidyl ether of 2,2,5,5-tetramethylolcyclopentanone 102 parts of tetramethylolcyclopentanone are dissolved in 500 parts of dioxane at 100° C. There are then added, with stirring and refluxing, 10 parts of $SnCl_4$ and 185 parts of epichlorohydrin. The latter is added dropwise in such a manner that the dioxane solution continuously boils without external heating. The reaction mixture is then refluxed for a further 2 hours. The dioxane is distilled off, and the residue is dissolved in 750 parts by volume of toluene. In the course of azeotropic water separation, there are added, at 55° C. and 0.15 bar, 176 parts of a 50% aqueous sodium hydroxide solution, and distillation is continued for 30 minutes after completion of the addition of sodium hydroxide solution. The formed product is freed from sodium chloride by washing with water; the pH value of the product is adjusted to 5–6 with 5% aqueous $NaHSO_4$, and it is finally dried over $Na_2SO_4$. The toluene is distilled off under reduced pressure to thus obtain the product in the form of a red resin.

| yield: | 136.5 parts (64% of theory) |
|---|---|
| epoxide content: | 5.35 equiv./kg. |

EXAMPLE 5

Tetraglycidyl ether of 4-methyl-2,2,6,6-tetramethylolcyclohexanol

According to the procedure of Example 2, 80 parts of 4-methyl-2,2,6,6-tetramethylolcyclohexanol are reacted, in the presence of 11 parts of 50% aqueous tetramethylammonium chloride, with 1375 parts of epichlorohydrin and 163.6 parts of a 50% sodium hydroxide solution. The product obtained is in the form of a yellowish oil.

| yield: | 138.1 parts (81% of theory) |
|---|---|
| viscosity at 25° C.: | 3.4 Pa · s |
| epoxide content: | 7.0 equiv./kg |
| $Cl_{total}$: | 4.2% |
| $Cl_{hydrolysable}$: | 0.57%. |

APPLICATION EXAMPLES

EXAMPLE A 100 parts by weight of tetraglycidyl ether, produced according to Example 1, are mixed with 46 parts of a curing agent. The curing agent is a polyamine adduct curing agent and is composed of 28 parts of bisphenol-A-diglycidyl ether, 57.7 parts of trimethylhexamethylenediamine and 14.3 parts of phenol. The mixture has a pot life of 10–15 minutes at an ambient temperature of 20° C. with 65% relative humidity. A 200$\mu$ thick film fully cures within 3 hours under these conditions. After storage for 7 days at room temperature, there is obtained a film which is resistant to acetone, methyl ethyl ketone, ethyl acetate, toluene and xylene.

| hardness according to Persoz: | 300 sec. |
|---|---|
| cupping test value (DIN 53156): | 6 mm. |

EXAMPLE B 100 parts of tetraglycidyl ether according to Example 2 and 95.5 parts of hexahydrophthalic anhydride are mixed; the mixture is poured into moulds of 150×150×4 mm and cured for 12 hours at 120° C. and for 6 hours at 140° C. There are thus obtained light-yellow, tough and fully satisfactory plates, which are then cut up into test specimens. The following mechanical properties are subsequently determined:

| flexural strength (ISO 178): | 100 N/mm$^2$ |
|---|---|
| edge-fibre elongation (ISO 178): | 5.7% |
| impact bend strength (VSM 77105): | 11.5 kJ/m$^2$ |
| thermal stability under load according to Martens: | 154° C. |
| boiling-water absorption (1 h at 100° C.): | 0.32%. |

EXAMPLE C 100 parts of tetraglycidyl ether, produced according to Example 1, are mixed with 125 parts of a curing agent. The curing agent is a commercially obtainable, modified polyamidoamine curing agent having the following characteristic properties:

| amine content: | 200–225 |
|---|---|
| viscosity at 25° C.: | 3000–6500 mPa · s |
| solids content: | 100% |
| colour value according to Gardener and Holt: | about 12 |
| flash point: | >200° C. |

The tetraglycidyl ether/curing agent mixture is cured at 25° C. for 7 days, and is subsequently applied to cold-rolled steel plates. The coated plates are then irradiated for 1000 hours with a xenon-arc weatherometer, and the gloss retention value at 60° C. is measured at specific intervals of time (ASTM* D-523). The results are summarised in the Table below.

* ASTM = American Society for Testing and Materials.

TABLE

| | GLOSS RETENTION AT 60° C. after the following hours of irradiation | | | | | | | | | | |
|---|---|---|---|---|---|---|---|---|---|---|---|
| | 0 | 100 | 200 | 300 | 400 | 500 | 600 | 700 | 800 | 900 | 1000 |
| coating according to Example C | 88 | 90 | 87 | 91 | 80 | 89 | 85 | 91 | 81 | 81 | 93 |

It is seen from the Table that the gloss retention value remain practically constant over a period of 1000 hours.

What is claimed is:

1. A tetraglycidyl ether of the formula I

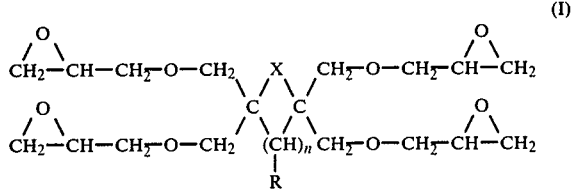

wherein X is a group

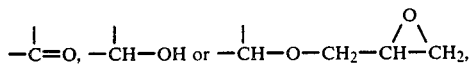

R is hydrogen or methyl, and n is an integer from 2 to 4.

2. A tetraglycidyl ether according to claim 1, wherein X is the group

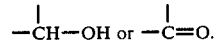

3. A tetraglycidyl ether according to claim 1, wherein R is hydrogen.

4. A tetraglycidyl ether according to claim 1, wherein n is 2 or 3.

5. A tetraglycidyl ether according to claim 1, which is the tetraglycidyl ether of 2,2,6,6-tetramethylolcyclohexanol.

6. A tetraglycidyl ether according to claim 1, which is the tetraglycidyl ether of 2,2,6,6-tetramethylolcyclohexanone.

7. A tetraglycidyl ether according to claim 1, which is the tetraglycidyl ether of 2,2,5,5-tetramethylolcyclopentanone.

8. A tetraglycidyl ether according to claim 1, which is the tetraglycidyl ether of 4-methyl-2,2,6,6-tetramethylolcyclohexanol.

9. A curable mixture containing a tetraglycidyl ether according to claim 1, and a curing agent for epoxide resins.

* * * * *